(12) United States Patent
Rieping

(10) Patent No.: US 8,030,019 B2
(45) Date of Patent: *Oct. 4, 2011

(54) PROCESS FOR L-AMINO ACID PRODUCTION USING ENTEROBACTERIACEAE WITH OVER-EXPRESSION OF PTSG GENE

(75) Inventor: Mechthild Rieping, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 923 days.

This patent is subject to a terminal disclaimer.

(21) Appl. No.: 11/946,120

(22) Filed: Nov. 28, 2007

(65) Prior Publication Data

US 2009/0226985 A1  Sep. 10, 2009

Related U.S. Application Data

(63) Continuation of application No. 10/481,743, filed as application No. PCT/EP02/06563 on Jun. 14, 2002, now Pat. No. 7,320,882.

(60) Provisional application No. 60/303,790, filed on Jul. 10, 2001.

(30) Foreign Application Priority Data

Jul. 6, 2001 (DE) .................................. 101 32 946

(51) Int. Cl.
*C12P 1/00* (2006.01)
*C12N 1/12* (2006.01)
(52) U.S. Cl. ........................................ 435/41; 435/252.1
(58) Field of Classification Search .................. None
See application file for complete search history.

(56) References Cited

U.S. PATENT DOCUMENTS

| 4,278,765 A | 7/1981 | Debabov et al. .............. 435/481 |
| 5,705,371 A | 1/1998 | Debabov et al. .............. 435/115 |

OTHER PUBLICATIONS

Notley-McRobb et al. (2000) Journal of Bacteriology, vol. 182, p. 4437-4442.
Bouma et al. (1987) Proc. Natl. Acad. Sci. USA, vol. 84, p. 930-934.
Erni et al. (1982) The Journal of Biological Chemistry, vol. 257, p. 13726-13730.
Theze et al. (1974) Journal of Bacteriology, vol. 118, p. 990-998.

*Primary Examiner* — Alexander Kim
(74) *Attorney, Agent, or Firm* — Smith, Gambrell & Russell, LLP

(57) ABSTRACT

The invention relates to a process for the preparation of L-amino acids, in particular L-threonine.

11 Claims, 1 Drawing Sheet

```
                        SEQUENCE LISTING

<160> NUMBER OF SEQ ID NOS: 2

<210> SEQ ID NO 1
<211> LENGTH: 25
<212> TYPE: DNA
<213> ORGANISM: Escherichia coli

<400> SEQUENCE: 1
cgtaaatcta gaacccatac ttagg                                          25

<210> SEQ ID NO 2
<211> LENGTH: 23
<212> TYPE: DNA
<213> ORGANISM: Escherichia coli

<400> SEQUENCE: 2
cctaagcttc cccaacgtct tac                                            23
```

PROCESS FOR L-AMINO ACID PRODUCTION USING ENTEROBACTERIACEAE WITH OVER-EXPRESSION OF PTSG GENE

This application is a continuation of U.S. patent application Ser. No. 10/481,743, filed 7 May 2004 now U.S. Pat. No. 7,320,882, allowed, which is a 371 application of PCT/EP02/06563, filed 14 Jun. 2002, which claims the benefit of U.S. Provisional Application Ser. No. 60/303,790, filed 10 Jul. 2001, and claims the benefit of DE 101 32 946.6 filed 6 Jul. 2001, all of which are herein incorporated by reference in their entirety.

FIELD OF THE INVENTION

This invention relates to a process for the preparation of L-amino acids, in particular L-threonine, using strains of the Enterobacteriaceae family in which at least the ptsG gene is enhanced.

PRIOR ART

L-Amino acids, in particular L-threonine, are used in human medicine and in the pharmaceuticals industry, in the foodstuffs industry and very particularly in animal nutrition.

It is known to prepare L-amino acids by fermentation of strains of Enterobacteriaceae, in particular *Escherichia coli* (*E. coli*) and *Serratia marcescens*. Because of their great importance, work is constantly being undertaken to improve the preparation processes. Improvements to the process can relate to fermentation measures, such as e.g. stirring and supply of oxygen, or the composition of the nutrient media, such as e.g. the sugar concentration during the fermentation, or the working up to the product form, by e.g. ion exchange chromatography, or the intrinsic output properties of the microorganism itself.

Methods of mutagenesis, selection and mutant selection are used to improve the output properties of these microorganisms. Strains which are resistant to antimetabolites, such as e.g. the threonine analogue α-amino-β-hydroxyvaleric acid (AHV), or are auxotrophic for metabolites of regulatory importance and produce L-amino acid, such as e.g. L-threonine, are obtained in this manner.

Methods of the recombinant DNA technique have also been employed for some years for improving the strain of strains of the Enterobacteriaceae family which produce L-amino acids, by amplifying individual amino acid biosynthesis genes and investigating the effect on the production.

OBJECT OF THE INVENTION

The object of the invention is to provide new measures for improved fermentative preparation of L-amino acids, in particular L-threonine.

SUMMARY OF THE INVENTION

The invention provides a process for the preparation of L-amino acids, in particular L-threonine, using microorganisms of the Enterobacteriaceae family which in particular already produce L-amino acids and in which the nucleotide sequence which codes for the ptsG gene is enhanced.

DETAILED DESCRIPTION OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Threonine is particularly preferred.

The term "enhancement" in this connection describes the increase in the intracellular activity of one or more enzymes or proteins in a microorganism which are coded by the corresponding DNA, for example by increasing the number of copies of the gene or genes, using a potent promoter or a gene or allele which codes for a corresponding enzyme or protein with a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The process is characterized in that the following steps are carried out:
a) fermentation of microorganisms of the Enterobacteriaceae family in which the ptsG gene is enhanced,
b) concentration of the corresponding L-amino acid in the medium or in the cells of the microorganisms of the Enterobacteriaceae family, and
c) isolation of the desired L-amino acid, constituents of the fermentation broth and/or the biomass in its entirety or portions (>0 to 100%) thereof optionally remaining in the product.

The microorganisms which the present invention provides can produce L-amino acids from glucose, sucrose, lactose, fructose, maltose, molasses, optionally starch, optionally cellulose or from glycerol and ethanol. They are representatives of the Enterobacteriaceae family chosen from the genera *Escherichia*, *Erwinia*, *Providencia* and *Serratia*. The genera *Escherichia* and *Serratia* are preferred. Of the genus *Escherichia* the species *Escherichia coli* and of the genus *Serratia* the species *Serratia marcescens* are to be mentioned in particular.

Suitable strains, which produce L-threonine in particular, of the genus *Escherichia*, in particular of the species *Escherichia coli*, are, for example
  *Escherichia coli* TF427
  *Escherichia coli* H4578
  *Escherichia coli* KY10935
  *Escherichia coli* VNIIgenetika MG442
  *Escherichia coli* VNIIgenetika M1
  *Escherichia coli* VNIIgenetika 472T23
  *Escherichia coli* BKIIM B-3996
  *Escherichia coli* kat 13
  *Escherichia coli* KCCM-10132.

Suitable L-threonine-producing strains of the genus *Serratia*, in particular of the species *Serratia marcescens*, are, for example
  *Serratia marcescens* HNr21
  *Serratia marcescens* TLr156
  *Serratia marcescens* T2000.

Strains from the Enterobacteriaceae family which produce L-threonine preferably have, inter alia, one or more genetic or phenotypic features chosen from the group consisting of: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to rifampicin, resistance to valine analogues, such as, for example, valine hydroxamate, resistance to purine analogues, such as, for example, 6-dimethylaminopurine, a need for L-methionine, optionally a partial and compensable need for L-isoleucine, a need for meso-diaminopimelic acid, auxotrophy in respect of threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally an ability for sucrose utilization, enhancement of the threonine operon, enhancement of homoserine dehydrogenase I-aspartate kinase I, preferably of the feed back resistant form, enhancement of homoserine kinase, enhancement of threonine synthase, enhancement of aspartate kinase, optionally of the feed back resistant form, enhancement of aspartate semialdehyde dehydrogenase, enhancement of phosphoenol pyruvate carboxylase, optionally of the feed back resistant form, enhancement of phosphoenol pyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

It has been found that microorganisms of the Enterobacteriaceae family produce L-amino acids, in particular L-threonine, in an improved manner after enhancement, in particular over-expression, of the ptsG gene.

The use of endogenous genes is in general preferred. "Endogenous genes" or "endogenous nucleotide sequences" are understood as meaning the genes or nucleotide sequences present in the population of a species.

The nucleotide-sequences of the genes of *Escherichia coli* belong to the prior art and can also be found in the genome sequence of *Escherichia coli* published by Blattner et al. (Science 277: 1453-1462 (1997)).

The following information on the ptsG gene is known, inter alia, from the prior art:
Description: Glucose-specific IIBC component of the phosphotransferase system (PTS)
EC No.: 2.7.1.69
Reference: Erni and Zanolari; Journal of Biological Chemistry. 261(35): 16398-16403 (1986) Bouma et al.; Proceedings of the National Academy of Sciences USA 84(4): 930-934 (1987) Meins et al.; Journal of Biological Chemistry 263(26): 12986-12993 (1988)
Accession No.: AE000210
Alternative gene names: CR, car, cat, gpt, umg, glcA The nucleic acid sequences can be found in the databanks of the National Center for Biotechnology Information (NCBI) of the National Library of Medicine (Bethesda, Md., USA), the nucleotide sequence databank of the European Molecular Biologies Laboratories (EMBL, Heidelberg, Germany or Cambridge, UK) or the DNA databank of Japan (DDBJ, Mishima, Japan).

Alleles of the ptsG gene which result from the degeneracy of the genetic code or due to "sense mutations" of neutral function can furthermore be used.

To achieve an enhancement, for example, expression of the genes or the catalytic properties of the proteins can be increased. The two measures can optionally be combined.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-threonine production. The expression is likewise improved by measures to prolong the life of the m-RNA. Furthermore, the enzyme activity is also enhanced by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Chang and Cohen (Journal of Bacteriology 134: 1141-1156 (1978)), in Hartley and Gregori (Gene 13: 347-353 (1981)), in Amann and Brosius (Gene 40: 183-190 (1985)), in de Broer et al. (Proceedings of the National Academy of Sciences of the United States of America 80: 21-25 (1983)), in LaVallie et al. (BIO/TECHNOLOGY 11: 187-193 (1993)), in PCT/US97/13359, in Llosa et al. (Plasmid 26: 222-224 (1991)), in Quandt and Klipp (Gene 80: 161-169 (1989)), in Hamilton (journal of Bacteriology 171: 4617-4622 (1989)), in Jensen and Hammer (Biotechnology and Bioengineering 58: 191-195 (1998)) and in known textbooks of genetics and molecular biology.

Plasmid vectors which are capable of replication in Enterobacteriaceae, such as e.g. cloning vectors derived from pACYC184 (Bartolomé et al.; Gene 102: 75-78 (1991)), pTrc99A (Amann et al.; Gene 69: 301-315 (1988)) or pSC101 derivatives (Vocke and Bastia, Proceedings of the National Academy of Sciences USA 80(21): 6557-6561 (1983)) can be used. A strain transformed with a plasmid vector, wherein the plasmid vector carries at least one nucleotide sequence which codes for the ptsG gene, can be employed in a process according to the invention.

It is also possible to transfer mutations which affect the expression of the particular gene into various strains by sequence exchange (Hamilton et al. (Journal of Bacteriology 171: 4617-4622 (1989)), conjugation or transduction.

It may furthermore be advantageous for the production of L-amino acids, in particular L-threonine, with strains of the Enterobacteriaceae family to enhance one or more enzymes of the known threonine biosynthesis pathway or enzymes of anaplerotic metabolism or enzymes for the production of reduced nicotinamide adenine dinucleotide phosphate, in addition to the enhancement of the ptsG gene.

Thus, for example, one or more of the genes chosen from the group consisting of
the thrABC operon which codes for aspartate kinase, homoserine dehydrogenase, homoserine kinase and threonine synthase (U.S. Pat. No. 4,278,765),
the pyc gene which codes for pyruvate carboxylase (DE-A-19 831 609),
the pps gene which codes for phosphoenol pyruvate synthase (Molecular and General Genetics 231(2): 332-336 (1992)),
the ppc gene which codes for phosphoenol pyruvate carboxylase (Gene 31: 279-283 (1984)),
the pntA and pntB genes which code for transhydrogenase (European Journal of Biochemistry 158: 647-653 (1986)),
the rhtB gene which imparts homoserine resistance (EP-A-0 994 190),
the mqo gene which codes for malate:quinone oxidoreductase (WO 02/06459),
the rhtc gene which imparts threonine resistance (EP-A-1 013 765),
the thrE gene of *Corynebacterium glutamicum* which codes for the threonine export protein (WO 01/92545), the gdhA gene which codes for glutamate dehydrogenase (Nucleic Acids Research 11: 5257-5266 (1983); Gene 23: 199-209 (1983)), the hns gene which codes for the DNA-binding protein HLP-II (Molecular and General Genetics 212(2): 199-202 (1988), Accession No. AE000222), the lrp gene which codes for the regulator of the leucine Lrp regulon and high-affinity transport systems of branched-chain amino acids (Journal of Biological Chemistry 266 (17): 10768-10774 (1991), Accession No. AE000191), the pgm gene which codes for phosphoglucomutase (Journal of Bacteriology 176: 5847-5851 (1994), Accession No. AE000172), the fba gene which codes for fructose bisphosphate aldolase (Biochemical Journal 257: 529-534 (1989), Accession No. AE000376), the dps gene which codes for the global regulator Dps (Genes & Development 6(12B): 2646-2654 (1992), Accession No. AE000183), the ptsH gene of the ptsHIcrr operon which codes for the phosphohistidine protein hexose phosphotransferase of the phosphotransferase system PTS (Journal of Biological Chemistry 262(33): 16241-16253 (1987), Accession No. AE000329), the ptsI gene of the ptsHIcrr operon which codes for enzyme I of the phosphotransferase system PTS (Journal of Biological Chemistry 262(33): 16241-16253 (1987), Accession No. AE000329), the crr gene of the ptsHIcrr operon which codes for the glucose-specific IIA component of the phosphotransferase system PTS (Journal of Biological Chemistry 262(33): 16241-16253 (1987), Accession No. AE000329), the mopB gene which codes for chaperone GroES (Journal of Biological Chemistry 261(26): 12414-12419 (1986), Accession No. AE000487), the ahpc gene of the ahpCF operon which codes for the small subunit of alkyl hydroperoxide reductase (Proceedings of the National Academy of Sciences USA 92(17): 7617-7621 (1995), Accession No. AE000166), the ahpF gene of the ahpCF operon which codes for the large subunit of alkyl hydroperoxide reductase (Proceedings of the National Academy of Sciences USA 92(17): 7617-7621 (1995), Accession No. AE000166), can be enhanced, in particular over-expressed.

The use of endogenous genes is in general preferred.

It may furthermore be advantageous for the production of L-amino acids, in particular L-threonine, in addition to the enhancement of the ptsG gene, for one or more of the genes chosen from the group consisting of the tdh gene which codes for threonine dehydrogenase (Journal of Bacteriology 169: 4716-4721 (1987)), the mdh gene which codes for malate dehydrogenase (E.C. 1.1.1.37) (Archives in Microbiology 149: 36-42 (1987)), the gene product of the open reading frame (orf) yjfA (Accession Number AAC77180 of the National Center for Biotechnology Information (NCBI, Bethesda; MD, USA)), the gene product of the open reading frame (orf) ytfP (Accession Number AAC77179 of the National Center for Biotechnology Information (NCBI, Bethesda, Md., USA)), the pckA gene which codes for the enzyme phosphoenol pyruvate carboxykinase (Journal of Bacteriology 172: 7151-7156 (1990)), the poxB gene which codes for pyruvate oxidase (Nucleic Acids Research 14(13): 5449-5460 (1986)), the aceA gene which codes for the enzyme isocitrate lyase (Journal of Bacteriology 170: 4528-4536 (1988)), the dgsA gene which codes for the DgsA regulator of the phosphotransferase system (Bioscience, Biotechnology and Biochemistry 59: 256-251 (1995)) and is also known under the name of the mlc gene, the fruR gene which codes for the fructose repressor (Molecular and General Genetics 226: 332-336 (1991)) and is also known under the name of the cra gene, and the rpoS gene which codes for the sigma$^{38}$ factor (WO 01/05939) and is also known under the name of the katF gene, to be attenuated, in particular eliminated or for the expression thereof to be reduced.

The term "attenuation" in this connection describes the reduction or elimination of the intracellular activity of one or more enzymes (proteins) in a microorganism which are coded by the corresponding DNA, for example by using a weak promoter or a gene or allele which codes for a corresponding enzyme with a low activity or inactivates the corresponding enzyme (protein) or gene, and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

It may furthermore be advantageous for the production of L-amino acids, in particular L-threonine, in addition to the enhancement of the ptsG gene, to eliminate undesirable side reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention can be cultured in the batch process (batch culture), the fed batch (feed process) or the repeated fed batch process (repetitive feed process). A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren und periphere Einrichtungen [Bioreactors and Peripheral Equipment] (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American. Society for Bacteriology (Washington D.C., USA, 1981).

Sugars and carbohydrates, such as e.g. glucose, sucrose, lactose, fructose, maltose, molasses, starch and optionally cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 25° C. to 45° C., and preferably 30° C. to 40° C. Culturing is continued until a maximum of L-amino acids or L-threonine has formed. This target is usually reached within 10 hours to 160 hours.

The analysis of L-amino acids can be carried out by anion exchange chromatography with subsequent ninhydrin derivation, as described by Spackman et al. (Analytical Chemistry 30: 1190-1206 (1958), or it can take place by reversed phase HPLC as described by Lindroth et al. (Analytical Chemistry 51: 1167-1174 (1979)).

The process according to the invention is used for the fermentative preparation of L-amino acids, such as, for example, L-threonine, L-isoleucine, L-valine, L-methionine, L-homoserine and L-lysine, in particular L-threonine.

The present invention is explained in more detail in the following with the aid of embodiment examples.

The minimal (M9) and complete media (LB) for *Escherichia coli* used are described by J. H. Miller (A Short Course in Bacterial Genetics (1992), Cold Spring Harbor Laboratory Press). The isolation of plasmid DNA from *Escherichia coli* and all techniques of restriction, ligation, Klenow and alkaline phosphatase treatment are carried out by the method of Sambrook et al. (Molecular Cloning—A Laboratory Manual (1989) Cold Spring Harbor Laboratory Press). Unless described otherwise, the transformation of *Escherichia coli* is carried out by the method of Chung et al. (Proceedings of the National Academy of Sciences of the United States of America (1989) 86: 2172-2175).

The incubation temperature for the preparation of strains and transformants is 37° C.

EXAMPLE 1

Construction of the Expression Plasmid pTrc99AptsG

The ptsG gene from *E. coli* K12 is amplified using the polymerase chain reaction (PCR) and synthetic oligonucleotides. Starting from the nucleotide sequence of the ptsG gene in *E. coli* K12 MG1655 (Accession Number AE000210, Blattner et al. (Science 277: 1453-1462 (1997)), PCR primers are synthesized (MWG Biotech, Ebersberg, Germany). The sequences of the primers are modified such that recognition sites for restriction enzymes are formed. The recognition sequence for XbaI is chosen for the ptsG1 primer and the recognition sequence for HindIII for the ptsG2 primer, which are marked by underlining in the nucleotide sequence shown below:

```
                                         (SEQ ID No. 1)
    ptsG1:  5' - CGTAAATCTAGAACCCATACTTGG - 3'

(SEQ ID No. 2)
    ptsG2:  5' - CCTAAGCTTCCCCAACGTCTTAC - 3'
```

The chromosomal *E. coli* K12 MG1655 DNA employed for the PCR is isolated according to the manufacturer's instructions with "Qiagen Genomic-tips 100/G" (QIAGEN, Hilden, Germany). A DNA fragment approx. 1500 bp in size can be amplified with the specific primers under standard PCR conditions (Innis et al. (1990) PCR Protocols. A Guide to Methods and Applications, Academic Press) with Pfu-DNA polymerase (Promega Corporation, Madison, USA). The PCR product is cleaved with the restriction enzymes XbaI and HindIII and ligated with the vector pTrc99A (Pharmacia Biotech, Uppsala, Sweden), which has been digested with the enzymes XbaI and HindIII. The *E. coli* strain XL1-Blue MRF' (Stratagene, La Jolla, USA) is transformed with the ligation batch and plasmid-carrying cells are selected on LB agar, to which 50 µg/ml ampicillin are added. Successful cloning can be demonstrated after plasmid DNA isolation by control cleavage with the enzymes KpnI and PvuI. The plasmid is called pTrc99AptsG (FIG. 1).

EXAMPLE 2

Preparation of L-threonine with the Strain MG442/pTrc99AptsG

The L-threonine-producing *E. coli* strain MG442 is described in the patent specification U.S. Pat. No. 4,278,765 and deposited as CMIM B-1628 at the Russian National Collection for Industrial Microorganisms (VKPM, Moscow, Russia).

The strain MG442 is transformed with the expression plasmid pTrc99AptsG described in example 1 and with the vector pTrc99A and plasmid-carrying cells are selected on LB agar with 50 µg/ml ampicillin. The strains MG442/pTrc99AptsG and MG442/pTrc99A are formed in this manner. Selected individual colonies are then multiplied further on minimal medium with the following composition: 3.5 g/l $Na_2HPO_4*2H_2O$, 1.5 g/l $KH_2PO_4$, 1 g/l $NH_4Cl$, 0.1 g/l $MgSO_4*7H_2O$, 2 g/l glucose, 20 g/l agar, 50 mg/l ampicillin. The formation of L-threonine is checked in batch cultures of 10 ml contained in 100 ml conical flasks. For this, 10 ml of preculture medium of the following composition: 2 g/l yeast extract, 10 g/l $(NH_4)_2SO_4$, 1 g/l $KH_2PO_4$, 0.5 g/l $MgSO_4*7H_2O$, 15 g/l $CaCO_3$, 20 g/l glucose, 50 mg/l ampicillin are inoculated and the batch is incubated for 16 hours at 37° C. and 180 rpm on an ESR incubator from Kuhner AG (Birsfelden, Switzerland). 250 µl portions of this preculture are transinoculated into 10 ml of production medium (25 g/l $(NH_4)_2SO_4$, 2 g/l $KH_2PO_4$, 1 g/l $MgSO_4*7H_2O$, 0.03 g/l $FeSO_4*7H_2O$, 0.018 g/l $MnSO_4*1H_2O$, 30 g/l $CaCO_3$, 20 g/l glucose, 50 mg/l ampicillin) and the batch is incubated for 48 hours at 37° C. For complete induction of the expression of the ptsG gene, 100 mg/l isopropyl β-D-thioglactopyranoside (IPTG) are added in parallel batches. The formation of L-threonine by the starting strain MG442 is investigated in the same manner, but no addition of ampicillin to the medium takes place. After the incubation the optical density (OD) of the culture suspension is determined with an LP2W photometer from Dr. Lange (Düsseldorf, Germany) at a measurement wavelength of 660 mm.

The concentration of L-threonine formed is then determined in the sterile-filtered culture supernatant with an amino acid analyzer from Eppendorf-BioTronik (Hamburg, Germany) by ion exchange chromatography and post-column reaction with ninhydrin detection.

The result of the experiment is shown in Table 1.

TABLE 1

| Strain | Additions | OD (660 nm) | L-Threonine g/l |
|---|---|---|---|
| MG442 | — | 5.6 | 1.4 |
| MG442/pTrc99A | — | 3.8 | 1.3 |
| MG442/pTrc99AptsG | — | 6.8 | 1.8 |
| MG442/pTrc99AptsG | IPTG | 5.7 | 2.3 |

Figure 1:
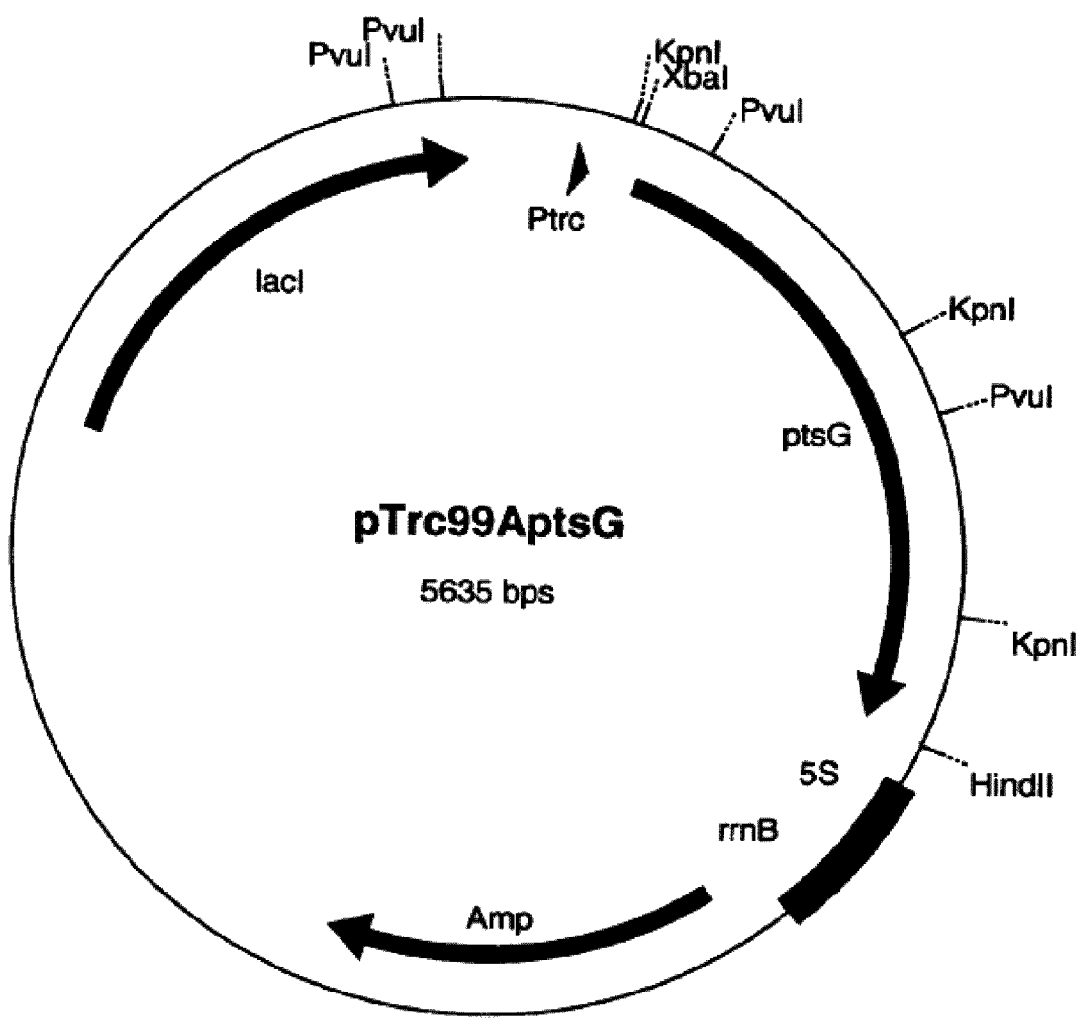
FIG. 1: Map of the plasmid pTrc99AptsG containing the ptsG gene.

The length data are to be understood as approx. data. The abbreviations and designations used have the following meaning:

| | |
|---|---|
| Amp: | Ampicillin resistance gene |
| lacI: | Gene for the repressor protein of the trc promoter |
| Ptrc: | trc promoter region, IPTG-inducible |
| ptsG: | Coding region of the ptsG gene |
| 5S: | 5S rRNA region |
| rrnBT: | rRNA terminator region |

The abbreviations for the restriction enzymes have the following meaning

HindIII: Restriction endonuclease from *Haemophilus influenzae*

KpnI: Restriction endonuclease from *Klebsiella pneumoniae*

PvuI: Restriction endonuclease from *Proteus vulgaris*

XbaI: Restriction endonuclease from *xanthomonas campestris*

What is claimed is:

1. A process for the preparation of L-amino acids in *Enterobacteriaceae*, comprising
  (a) fermenting, in a medium, *Enterobacteriaceae* which produce L-amino acid and in which the ptsG gene from *Escherichia coli* coding for glucose-specific IIBC component of the phosphotransferase system is over-expressed by placing the ptsG gene under a potent promoter,
  (b) concentrating the L-amino acids in the medium or in the *Enterobacteriaceae*, and
  (c) quantifying the L-amino acids.

2. The process according to claim 1, which further comprises increasing, in the *Enterobacteriaceae*, expression of a gene of the biosynthesis pathway of the L-amino acids.

3. The process according to claim 1, which further comprises reducing or eliminating, in the *Enterobacteriaceae*, expression of a gene of the metabolic pathway which reduces the amount of the L-amino acids.

4. The process according to claim 1, wherein the amount of the ptsG gene product is increased.

5. The process according to claim 1, wherein, expression of at least one gene selected from the group consisting of:
  (a) a thrABC operon which encodes aspartate kinase, homoserine dehydrogenase, homoserine kinase and threonine synthase,
  (b) a pyc gene which encodes pyruvate carboxylase,
  (c) a pps gene which encodes phosphoenol pyruvate synthase,
  (d) a ppc gene which encodes phosphoenol pyruvate carboxylase,
  (e) a pntA and pntB genes encode for transhydrogenase,
  (f) a rhtB gene which imparts homoserine resistance,
  (g) a mqo gene which encodes malate:quinone oxidoreductase,
  (h) a rhtC gene which imparts threonine resistance,
  (i) a thrE gene which encodes the threonine export protein,
  (j) a gdhA gene which encodes glutamate dehydrogenase, (k) a hns gene which encodes the DNA-binding protein HLP-II,
(l) a lrp gene which encodes the regulator of the leucine Lrp regulon,
(m) a pgm gene which encodes phosphoglucomutase,
(n) a fba gene which encodes the fructose bisphosphate aldolase,
(o) a dps gene which encodes the global regulator DPS,
(p) a ptsH gene which encodes the phosphohistidine protein hexose phosphotransferase,
(q) a ptsI gene which encodes enzyme I of the phosphotransferase system,
(r) a crr gene which encodes the glucose-specific IIA component,
(s) a mopB gene which encodes chaperone GroES,
(t) a ahpC gene which encodes the small sub-unit of alkyl hydroperoxide reductase, and
(u) a ahpF gene which encodes the large sub-unit of alkyl hydroperoxide reductase, is increased.

6. The process according to claim 5, wherein the ptsG gene and the fba gene are over-expressed.

7. A process according to claim 1, wherein, expression of at least one gene selected from the group consisting of:
(a) a tdh gene which encodes threonine dehydrogenase,
(b) a mdh gene which encodes malate dehydrogenase,
(c) a gene product of the open reading frame (orf) yjfA,
(d) a gene product of the open reading frame (orf) ytfp,
(e) a pckA gene which encodes phosphoenol pyruvate carboxykinase,
(f) a poxB gene which encodes pyruvate oxidase,
(g) a aceA gene which encodes isocitrate lyase,
(h) a dgsA gene which encodes the DgsA regulator of the phosphotransferase system,
(i) a fruR gene which encodes the fructose repressor, and
(j) a rpoS gene which encodes the sigma$^{38}$ factor is reduced.

8. The process according to claim 1, further comprising:
(c) isolating the L-amino acids.

9. The process according to claim 8, wherein at least a portion of constituents of the medium and/or a biomass resulting from fermenting remain with the isolated L-amino acids.

10. The process according to claim 1, wherein the L-amino acids are L-threonine.

11. The process according to claim 1, which further comprises increasing the copy number of the ptsG gene.

* * * * *